United States Patent [19]

Dougan et al.

[11] 4,041,942
[45] Aug. 16, 1977

[54] SURGICAL DRAPE

[75] Inventors: Ramon C. Dougan, Schaumburg, Ill.; Helen T. Rudtke, Medford, N.Y.

[73] Assignee: American Hospital Supply Corporation, Evanston, Ill.

[21] Appl. No.: 696,385

[22] Filed: June 15, 1976

[51] Int. Cl.² .......................................... A61F 13/00
[52] U.S. Cl. ............................................... 128/132 D
[58] Field of Search ................... 128/132 D, 292, 296

[56] References Cited

U.S. PATENT DOCUMENTS

| | | | |
|---|---|---|---|
| 3,916,447 | 11/1975 | Thompson | 128/132 D |
| 3,926,185 | 12/1975 | Krzewinski | 128/132 D |
| 3,930,497 | 1/1976 | Krebs et al. | 128/132 D |
| 3,956,048 | 5/1976 | Nordgren | 128/132 D |

Primary Examiner—Lawrence W. Trapp
Attorney, Agent, or Firm—Tilton, Fallon, Lungmus, Chestnut & Hill

[57] ABSTRACT

A drape for use in surgical procedures including a sterile sheet, a generally diamond-shaped opening in the sheet, and a slot extending from a corner of the opening to an edge of the sheet. The sheet is constructed of a disposable non-woven cellulosic material and the opening and the slot have folded edges formed by reversely folded portions of the material. A reinforcing sheet having a matching diamond-shaped opening and a matching slot can be secured to the main sheet in superimposed relation. The main sheet and the reinforcing sheet have respective openings and slots in direct alignment to define a fenestrated surgical drape having a pair of split end portions.

25 Claims, 8 Drawing Figures

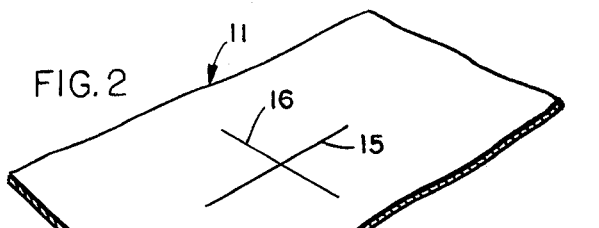
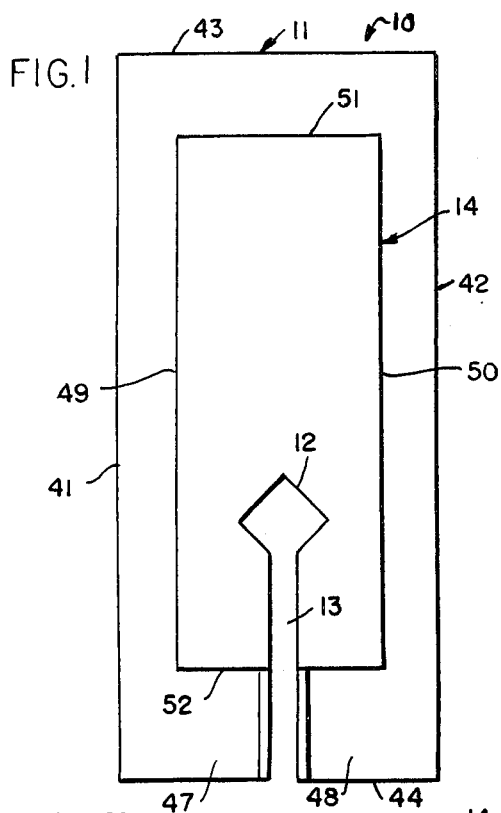
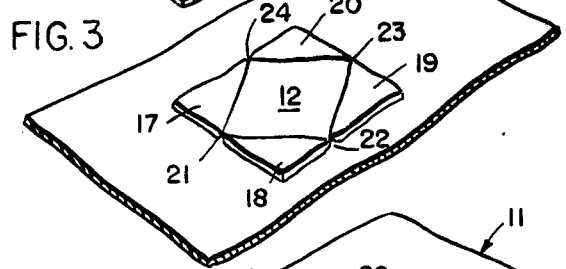
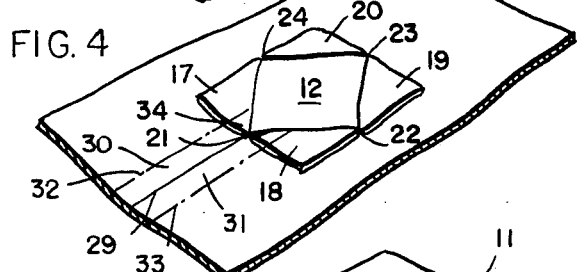
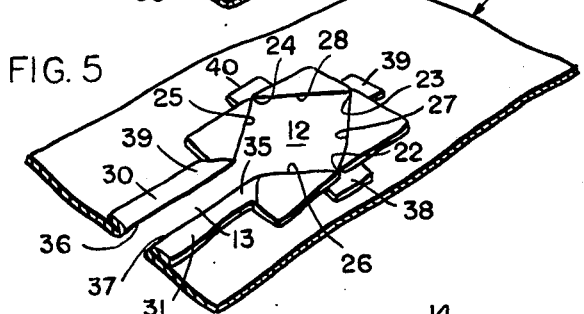
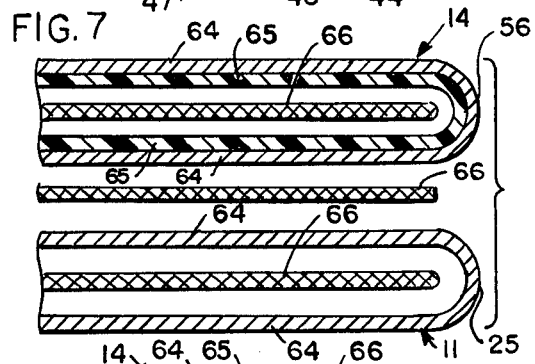
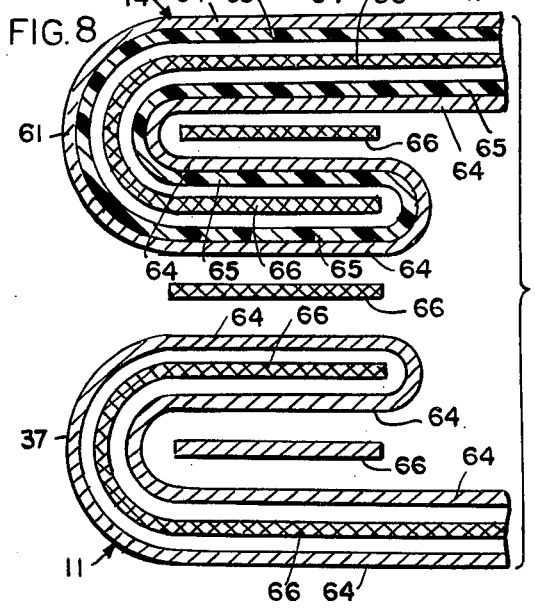
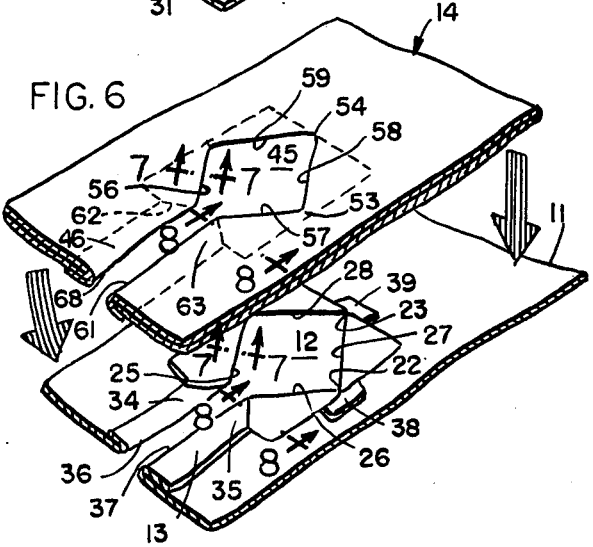

SURGICAL DRAPE

BACKGROUND

The present invention relates to surgical drapes and more particularly to fenestrated surgical drapes having split ends.

In recent years, surgical drapes formed primarily of non-woven cellulosic material have almost universally replaced the older and less satisfactory linen drapes. Such drapes have generally been considered far superior to linen drapes because of their effectiveness in blocking the passage of bacteria during use and their disposability after use. However, certain problems relating to contamination of the operative area have impeded the otherwise successful use of non-woven cellulosic material for the construction of surgical drapes.

The importance of surgical draping in providing an aseptic field about a central operative area is well known. It is common practice for many types of surgery to cover the patient and operating table with a sterile drape in such a way that only the portion of the body upon which surgery is to be performed is presented to the surgeon and his assistants. The drape must conform rather closely to the contour of the operative area to insure that a sterile surgical field is maintained until the procedure is completed. It is presently common practice to furnish one of several types of drape constructions and draping procedures in an effort to accomplish this objective. Nevertheless, surgical draping has not been providing the desired degree of nearly complete assurance against contamination of the operative area to effectively preclude post-operative infection.

In an effort to avoid such contamination problems, standard drapes and draping procedures have taken several forms. First, draping procedures have included the use of a standard drape by simply conforming an edge of the drape to the portion of the body upon which surgery is to be performed. This procedure has not proven to be fully satisfactory, however, because it has been difficult to closely conform the edge of a standard drape to the body to maintain a sterile surgical field. Second, draping procedures have included using a conventional laparotomy drape which is fenestrated but does not have split ends. Laparotomy drapes are not well suited for many surgical procedures such as craniotomies and orthopedic surgery, however, because the openings in such drapes generally cannot be made to closely conform to the head or the limb upon which surgery is to be performed to maintain a sterile surgical field. Third, draping procedures have included the use of a split drape by simply conforming a wide opening of the drape having die cut edges to the portion of the body upon which surgery is to be performed. This procedure has not proven to be fully satisfactory, however, because it has been difficult to keep small particles of material from entering the operative area to maintain a sterile surgical field. The three principle drapes and draping procedures heretofore used, particularly in orthopedic and craniotomy surgery, have therefore not been capable of fully utilizing the otherwise significant advantages of surgical drapes formed of non-woven cellulosic material.

The many advantages of surgical drapes formed of non-woven cellulosic material have lead to a search for ways to overcome the problem of contamination of the operative area by the drape constructions or draping procedures previously used. The result has been a number of drapes such as those disclosed in U.S. Pat. Nos. 3,926,185; 3,667,458; and 3,910,268, but such drapes have generally not been fully successful. The present invention represents a distinct improvement in a fenestrated surgical drape having split end portions which closely conforms to the portion of the body upon which surgery is to be performed and substantially eliminates the possibility of small particles of material entering the operative area to thereby effectively preclude post-operative infection from the drape construction or draping procedure.

SUMMARY

The present invention includes an improved drape for use in surgical procedures to maintain an aseptic field about the operative area. The surgical drape includes a sterile sheet of non-woven cellulosic material, a generally diamond-shaped opening in the sheet, and a slot extending from a corner of the opening to an edge of the sheet. The opening and the slot preferably have folded edges which are formed by reversely folding and adhesively bonding portions of the sheet. The sheet can advantageously be made generally rectangular in configuration with the reversely folded portions defining the opening being generally triangular and the reversely folded portions defining the slot being generally trapezoidal. The corners of the opening spaced from the slot preferably include reinforcing tabs with longitudinal and transverse reinforcing fibers extending through the non-woven cellulosic material of the sheet.

The surgical drape can also include a reinforcing sheet having a matching diamond-shaped opening and a matching slot secured to the main sheet in superimposed relation with the respective openings and slots in direct alignment. The reinforcing sheet is preferably formed of non-woven cellulosic material with a barrier film of liquid impermeable plastic material extending along the side of the reinforcing sheet facing the main sheet. The reinforcing sheet can advantageously be adhesively bonded to the main sheet with the reinforcing sheet covering a major portion of the main sheet. The reinforcing sheet and the main sheet preferably have pairs of spaced opposing obtusely angled corners disposed at the merger of the openings and the slots with the sheets having substantial thicknesses of material along the slots adjacent the opposing corners.

The present invention therefore retains the advantages inherent in surgical drapes formed of non-woven cellulosic material while adding the additional advantages of a fenestrated surgical drape having split end portions. The fenestration and the split end portions have folded edges to protect against small particles of material entering the operative area during surgical procedures to thereby effectively preclude this source of post-operative infection. The fenestration and the split end portions also facilitate closely conforming the drape to a variety of areas of the body upon which surgery may be performed.

It is, therefore, an object of the present invention to provide a fenestrated surgical drape with split ends formed of non-woven cellulosic material adapted for safe and effective use in a wide variety of surgical procedures. The provision of the surgical drape and the realization of the advantages derived therefrom constitute additional important objects of this invention. Other objects of the present invention can be appreciated from the details of construction and operation set forth in the accompanying specifications, claims and drawings.

DRAWINGS

The invention is described in conjunction with the accompanying drawings in which:

FIG. 1 is a plan view of a fenestrated surgical drape having split end portions in accordance with the present invention;

FIG. 2 is a fragmentary perspective view of a main sheet of the surgical drape with a cut therethrough for forming the fenestration;

FIG. 3 is a fragmentary perspective view of the main sheet of the surgical drape showing the reversely folded portions of the main sheet defining the fenestration;

FIG. 4 is a fragmentary perspective view of the main sheet of the surgical drape with a cut therethrough for forming the split end portions;

FIG. 5 is a fragmentary perspective view of the main sheet of the surgical drape showing the reversely folded portions of the main sheet defining the split end portions;

FIG. 6 is a fragmentary perspective view of a reinforcing sheet being placed on the main sheet in superimposed relation;

FIG. 7 is a cross-sectional view of the reinforcing hseet and the main sheet taken on the line 7—7 of FIG. 6; and FIG. 8 is a cross-sectional view of the reinforcing sheet and the main sheet taken on the line 8—8 of FIG. 6.

DESCRIPTION

In the illustration given and with reference first to FIG. 1, the numeral 10 designates generally a surgical drape in accordance with the present invention. The surgical drape 10 includes a sterile sheet 11 of non-woven cellulosic material, which is resistant to the passage of liquid therethrough, a generally diamond-shaped opening 12 in the sheet 11, and a slot 13 extending from a corner of the opening 12 to an edge of the sheet 11. An optional reinforcing sheet 14 is shown secured to the main sheet 11 in superimposed relation.

Referring to FIGS. 2 through 6, the surgical drape 10 of the present invention can be understood in greater detail. The opening 12 in the main sheet 10 is formed by first making a longitudinal cut 15 and a transverse cut 16 through the material (as shown in FIG. 2) at a location spaced inwardly from the edges of the sheet 11. The cuts 15 and 16 define generally triangular portions 17, 18, 19 and 20 which are reversely folded (as shown in FIG. 3) to form the generally diamond-shaped opening 12 having corners 21, 22, 23 and 24. The reversely folded portions 17, 18, 19 and 20 forming the opening 12 define folded edges 25, 26, 27 and 28.

The slot 13 in the sheet 11 is formed by first making a longitudinal cut 29 through the material (as shown in FIG. 4) which can suitably be an extension of the longitudinal cut 15 extending from the corner 21 of the opening 12 to the edge of the sheet 11. The cut 29 defines generally trapezoidal portions 30 and 31 which are reversely folded along the fold lines 32 and 33 to form the slot 13 having opposing corners 34 and 35. The reversely folded portions 26 and 27 forming the slot 13 define folded edges 36 and 37.

The reversely folded portions 17, 18, 19 and 20 around the opening 12 and the reversely folded portions 30 and 31 along the slot 13 are adhesively bonded to the sheet 11 with the exception of the opposing corners 34 and 35 of the reversely folded portions 30 and 31 which are adhesively bonded to the reversely turned portions 17 and 18. Thin plastic film reinforcing tabs 38, 39 and 40 are also adhesively bonded to the sheet 11 adjacent the corners 22, 23 and 24 of the opening 12 spaced from the slot 13. The non-woven cellulosic material of the sheet 11 with the adhesively bonded reversely folded portions 17, 18, 19, 20, 30, and 31 and the adhesively bonded reinforcing tabs 38, 39 and 40 provides strong resistance to forces tending to tear the opening 12 and the slot 13 during use of the drape 10.

The drape 10, which can include integral longitudinal and transverse reinforcing fibers, is preferably rectangular in configuration (as shown in FIG. 1) having a pair of opposing side edges 41 and 42 and a pair of opposing end edges 43 and 44. The slot 13 extends through the sheet 11 from the corner 21 of the opening 12 to the end edge 44. The drape 10 also preferably includes a reinforcing sheet 14 having a diamond-shaped opening 45 and a slot 46 (as shown in FIG. 6) which match the diamond-shaped opening 12 and the slot 13 in the main sheet 11. The main sheet 11 and the reinforcing sheet 14 are secured together in superimposed relation with their respective openings and slots in direct alignment. The aligned openings 45 and 12 define the fenestration and the aligned slots 46 and 13 define split end portions 47 and 48 of the drape 10.

The reinforcing sheet 14 is preferably formed of non-woven cellulosic material which includes a barrier film of liquid impermeable plastic material extending along the side of the reinforcing sheet 14 facing the main sheet 11. The details of construction of the opening 45 and the slot 46 in the reinforcing sheet 14 are preferably a mirror image (as shown in FIG. 6) of the construction of the opening 12 and the slot 13 in the main sheet 11. The reinforcing sheet 14 can then be adhesively boned to the main sheet 11 with the openings 45 and 12 and the slots 46 and 13 in direct alignment.

The reinforcing sheet 14 is also preferably rectangular in configuration (as shown in FIG. 1) having a pair of opposing side edges 49 and 50 and a pair of opposing end edges 51 and 52. The slot 46 in the reinforcing sheet 14 and the slot 13 in the main sheet 11 will then extend to corresponding end edges 52 and 44. The reinforcing sheet 14 so constructed preferably covers a major portion of the main sheet 11.

The reinforcing tabs 38, 39 and 40 are preferably adhesively bonded to both of the sheets when the reinforcing sheet 14 is used in conjunction with the main sheet 11. Since the reinforcing sheet 14 is placed on the main sheet 11 in superimposed relation, the corners 53, 54 and 55 of the opening 45 can then be secured to the corresponding corners 22, 23 and 24 of the opening 12 by the reinforcing tabs 38, 39 and 40. The reinforcing tabs 38, 39 and 40 will therefore provide strong resistance to forces tending to tear the corresponding corners of the openings 45 and 12 during use of the drape 10.

A pair of spaced opposing obtusely angled corners are defined by the merger of the opening 12 and the slot 13 in the main sheet 11. The main sheet 11 generally has a double thickness of material (as shown in FIG. 7) formed by the reversely folded portions along the slot 13 and around the opening 12. However, the main sheet 11 has a quadruple thickness of material (as shown in FIG. 8) along the slot 13 adjacent the opposing corners 34 and 35 formed by refolding folded integral portions of the material to define the slot 13 in the main sheet 11.

The opening 45 has folded edges 56, 57, 58 and 59 and the slot 46 has folded edges 60 and 61 formed by reversely folding integral portions of the reinforcing sheet 14 in mirror image fashion with respect to the main sheet 11. The reversely folded portions of the reinforcing sheet 14 preferably face the corresponding reversely folded portions of the main sheet 11. The reinforcing sheet 14 can then be adhesively bonded to the main sheet 11 in superimposed relation with the corresponding reversely folded portions of the openings and slots all in direct alignment.

A pair of spaced opposing obtusely angled corners are likewise defined by the merger of the opening 45 and the slot 46 in the reinforcing sheet 14. The reinforcing sheet 14 generally has a quadruple thickness of material (as shown in FIG. 7) formed by the reversely folded portions along the slot 46 and around the opening 45. However, the reinforcing sheet 14 has a double quadruple thickness of material (as shown in FIG. 8) along the slot 46 adjacent opposing corners 62 and 63 formed by refolding folded integral portions of the material to define the slot 46 in the reinforcing sheet 14.

Referring to FIG. 7, representative corresponding folded edges 25 and 56 of the main sheet 11 and the reinforcing sheet 14 can be better understood. The reinforcing sheet 14 includes a layer of non-woven cellulosic material 64 with a barrier film 65 of liquid impermeable plastic material extending along one side thereof and the folded edge 56 is formed by reversely folding a portion of the reinforcing sheet 14 and securing the reversely folded portion with an adhesive 66. The reversely folded portion provides a quadruple thickness of material consisting of a double layer of non-woven cellulosic material 64 and a double layer of barrier film 65.

The main sheet 11 includes a layer of non-woven cellulosic material 64 and the folded edge 32 is likewise formed by reversely folding a portion of the main sheet 11 and securing the reversely folded portion with an adhesive 66. The reversely folded portion provides a double thickness of material consisting of a double layer of non-woven cellulosic material 64. The reversely folded portions forming the folded edges of the reinforcing sheet can then be secured to the reversely folded portions forming the main sheet as the main sheet is bonded with an adhesive to the reinforcing sheet.

Referring to FIG. 8, representative corresponding folded edges 37 and 61 adjacent corresponding corners 35 and 63 of the main sheet 11 and the reinforcing sheet 14 can be better understood. The folded edge 61 adjacent the corner 63 is formed by refolding folded integral portions of the reinforcing sheet 14, which are already secured with an adhesive 66, to define the slot 46. The refolded portion provides two quadruple thicknesses of material. The first quadruple thickness of material includes a double layer of non-woven cellulosic material 64 and a double layer of barrier film 65. The first quadruple thickness of material is secured with an adhesive 66 to the second quadruple thickness of material. The second quadruple thickness of material again includes a double layer of non-woven cellulosic material 64 and a double layer of barrier film 65.

The folded edge 37 adjacent the corner 31 is likewise formed by refolding folded integral portions of the main sheet 11, which are already secured with an adhesive 66 to define the slot 13. The refolded portion provides two double thicknesses of material. The first double thickness of material includes a double layer of non-woven cellulosic material 64. The first double thickness of material is secured with an adhesive 66 to the second double thickness of material. The second double thickness of material again includes a double layer of non-woven cellulosic material 64. The refolded folded integral portions forming the folded edges of the reinforcing sheet 14 adjacent opposing corners 62 and 63 can then be secured to the refolded folded integral portions forming the folded edges of the main sheet adjacent opposing corners 34 and 35 as the main sheet is bonded with an adhesive to the reinforcing sheet.

The present invention, therefore, provides a surgical drape having a main sheet of non-woven cellulosic material with a diamond-shaped opening in the sheet and a slot extending from a corner of the opening to an edge of the sheet. The opening and the slot preferably have folded edges to protect against small particles of material entering the operative area during surgical procedures to thereby eliminate this potential source of post-operative infection. A reinforcing sheet of non-woven cellulosic material can advantageously be secured to the main sheet in superimposed relation with mirror image details of construction. The reinforcing sheet preferably includes a barrier film of liquid impermeable plastic material along the side thereof facing the main sheet. The reinforcing sheet and the main sheet form a disposable surgical drape which is highly effective in blocking the passage of bacteria during use.

The generally diamond-shaped openings and the slots in the main sheet and the reinforcing sheet define a fenestrated drape having split end portions which are closely conformable to various portions of the body upon which surgery may be performed. The fenestration can be snugly wrapped around the operative area and the drape can be clamped in the area immediately adjacent the merger of the slots with the openings where there is a substantial thickness of material to resist tearing forces. The slots are quite narrow making it possible to further clamp the split end portions of the drape in overlapping relationship eliminating the need for an additional drape to cover the slots. The present invention provides a drape which overcomes the limitations inherent in prior drapes and draping procedures used for the purposes herein described that can quickly and easily be used for a wide variety of surgical procedures such as craniotomies and orthopedic surgery.

While in the foregoing specification a detailed description of the invention has been set forth for purposes of illustration, variations of the details herein given may be made by those skilled in the art without departing from the spirit and scope of the invention.

I claim:

1. A surgical drape comprising a sterile sheet of non-woven cellulosic material, a generally diamond-shaped opening in said sheet and a slot extending from a corner of said opening to an edge of said sheet.

2. The surgical drape of claim 1 in which said opening and said slot have folded edges.

3. The surgical drape of claim 2 in which said folded edges are formed by reversely folding portions of said sheet to define said opening and said slot.

4. The surgical drape of claim 3 in which the reversely folded portions defining said opening are generally triangular and the reversely folded portions defining said slot are generally trapezoidal.

5. The surgical drape of claim 3 in which the reversely folded portions are adhesively bonded to said sheet.

6. The surgical drape of claim 1 in which said sheet is rectangular in configuration and has a pair of opposing side edges and a pair of opposing end edges with said slot extending to one of said end edges.

7. The surgical drape of claim 1 in which a reinforcing tab is secured to said sheet adjacent each of the corners of said opening spaced from said slot.

8. The surgical drape of claim 1 in which said non-woven cellulosic material is resistant to the passage of liquid through said sheet.

9. The surgical drape of claim 1 in which said sheet includes longitudinal and transverse reinforcing fibers integral with said non-woven cellulosic material.

10. A sterile surgical drape comprising a main sheet of non-woven cellulosic material having a generally diamond-shaped opening therethrough and having a slot extending from a corner of said opening to an edge of said sheet, and a reinforcing sheet having a matching diamond-shaped opening and a matching slot, said main sheet and said reinforcing sheet being secured together in superimposed relation with their respective openings and slots in direct alignment, and said aligned openings together defining a fenestration through said drape and said slots dividing the portion of said drape between said fenestration and said edge into a pair of split end portions.

11. The sterile surgical drape of claim 10 in which said reinforcing sheet is formed of non-woven cellulosic material.

12. The sterile surgical drape of claim 11 in which said reinforcing sheet includes a barrier film of liquid impermeable plastic material extending along the side thereof facing said main sheet.

13. The sterile surgical drape of claim 10 in which said openings and said slots have folded edges.

14. The sterile surgical drape of claim 13 in which said folded edges are formed by reversely folding portions of said sheets to define said openings and said slots.

15. The sterile surgical drape of claim 14 in which the reversely folded portions defining said openings are generally triangular and the reversely folded portions defining said slots are generally trapezoidal.

16. The sterile surgical drape of claim 14 in which the reversely folded portions of said main sheet are adhesively bonded to said main sheet and the reversely folded portions of said reinforcing sheet are adhesively bonded to said reinforcing sheet.

17. The sterile surgical drape of claim 16 in which said reinforcing sheet is adhesively bonded to said main sheet.

18. The sterile surgical drape of claim 17 in which a reinforcing tab is secured to said sheets adjacent each of the corresponding corners of said openings spaced from said slots.

19. The sterile surgical drape of claim 18 in which said reinforcing tabs are a thin plastic film having pressure sensitive adhesive on both sides thereof for resisting forces tending to tear the corresponding corners of said openings.

20. The sterile surgical drape of claim 10 in which said sheets are rectangular in configuration and each of said sheets has a pair of opposing side edges and a pair of opposing end edges with said slots in said sheets extending to corresponding ones of said end edges.

21. The sterile surgical drape of claim 18 in which said reinforcing sheet covers a major portion of said main sheet.

22. The sterile surgical drape of claim 10 in which said opening and said slot of said main sheet have folded edges formed by reversely folding integral portions of said sheet, said reversely folded portions being disposed on the side of said main sheet facing said reinforcing sheet and being adhesively secured to said reinforcing sheet.

23. The sterile surgical drape of claim 22 in which said main sheet has a pair of spaced opposing obtusely angled corners disposed at the merger of said opening and said slot, said main sheet having quadruple thickness of material along said slot adjacent said opposing corners formed by refolding folded integral portions as said main sheet is folded to define said opening and said slot.

24. The sterile surgical drape of claim 23 in which said opening and said slot of said reinforcing sheet have folded edges formed by reversely folding integral portions of said sheet, said reversely folded portions being disposed on the side of said main sheet facing said reinforcing sheet and being adhesively secured to said reinforcing sheet.

25. The sterile surgical drape of claim 24 in which said reinforcing sheet has a pair of spaced opposing obtusely angled corners disposed at the merger of said opening and said slot, said reinforcing sheet having double quadruple thickness of material along said slot adjacent said opposing corners formed by refolding folded integral portions as said reinforcing sheet is folded to define said opening and said slot.

* * * * *